United States Patent
Dörr et al.

(10) Patent No.: US 10,907,078 B2
(45) Date of Patent: Feb. 2, 2021

(54) CONTACT ADHESIVE PRODUCT BASED ON POLYURETHANE RESIN, PRODUCTION THEREOF, AND CORRESPONDING CONTACT ADHESIVE

(71) Applicant: Covestro Deutschland AG, Leverkusen (DE)

(72) Inventors: Sebastian Dörr, Düsseldorf (DE); Marc-Stephan Weiser, Leverkusen (DE); Sascha Plug, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 201 days.

(21) Appl. No.: 16/312,027

(22) PCT Filed: Jun. 29, 2017

(86) PCT No.: PCT/EP2017/066197
§ 371 (c)(1),
(2) Date: Dec. 20, 2018

(87) PCT Pub. No.: WO2018/002257
PCT Pub. Date: Jan. 4, 2018

(65) Prior Publication Data
US 2019/0382635 A1 Dec. 19, 2019

(30) Foreign Application Priority Data
Jun. 30, 2016 (EP) .................................. 16177190

(51) Int. Cl.
*C09J 175/08* (2006.01)
*C08G 18/32* (2006.01)
(Continued)

(52) U.S. Cl.
CPC ........ *C09J 175/08* (2013.01); *C08G 18/3228* (2013.01); *C08G 18/755* (2013.01);
(Continued)

(58) Field of Classification Search
CPC .............. C09J 2201/60; C09J 2201/606; C09J 2201/622; C09J 175/02; C09J 175/04; C09J 175/06; C09J 175/08; C09J 175/10; C09J 175/12; C09J 7/38; C09J 7/20; C09J 7/201; C09J 7/203; C09J 7/205; C09J 7/21; C08L 2203/10; C08L 2201/54; C08L 2201/56; C08K 5/17; C08G 18/12; C08G 18/28; C08G 18/2805; C08G 18/281; C08G 18/2815; C08G 18/2825; C08G 18/283; C08G 18/2835; C08G 18/284; C08G 18/2845; C08G 18/285; C08G 18/2855; C08G 18/286; C08G 18/2865; C08G 18/2875; C08G 18/288; C08G 18/2885; C08G 18/289; C08G 18/40;
(Continued)

(56) References Cited

U.S. PATENT DOCUMENTS 4,288,586 A * 9/1981 Bock .................... C07D 251/34
528/44
5,692,937 A 12/1997 Zhang
(Continued)

FOREIGN PATENT DOCUMENTS

CN 104725589 A 6/2015
EP 2332998 A1 6/2011
(Continued)

OTHER PUBLICATIONS

International Search Report for PCT/EP2017/065894 dated Sep. 29, 2017.
International Search Report for PCT/EP2017/066197 dated Oct. 4, 2017.
Written Opinion of the International Searching Authority for PCT/EP2017/065894 dated Sep. 29, 2017.
Written Opinion of the International Searching Authority for PCT/EP2017/066197 dated Oct. 4, 2017.

*Primary Examiner* — Christopher M Rodd
(74) *Attorney, Agent, or Firm* — Faegre Drinker Biddle & Reath LLP

(57) ABSTRACT

The invention relates to a contact adhesive product, comprising a substrate and a polyurethane resin, which can be obtained by reacting at least A) an aliphatic polyisocyanate component having an average isocyanate functionality of ≥1.8 and ≤2.6, B) a polymeric polyether polyol component, C) an amino-functional chain extender component having at least 2 isocyanate-reactive amino groups, containing at least one amino-functional connection C1), which has no ionic or ionogenic group and/or an amino-functional compound C2), which has ionic or ionogenic groups, D) possibly further hydrophilic components which are different from C2), E) possibly hydroxy-functional compounds having a molecular weight of 62 to 399 mol/g, F) possibly further polymeric polyols which are different from B), G) a compound, which has precisely one isocyanate-reactive group, or a compound, which has more than one isocyanate-reactive group, wherein only one of the isocyanate-reactive groups reacts under the selected reaction conditions with the isocyanate groups present in the reaction mixture, and H) possibly an aliphatic polyisocyanate component having an average isocyanate functionality of >2.6 and ≤4, wherein the components B) and F) together contain ≤30 wt % on component F), based on the total mass of the components B) and F). The invention further relates to a method for producing the contact adhesive product, to a special polyurethane resin, and to a contact adhesive comprising said polyurethane resin.

15 Claims, No Drawings

(51) Int. Cl.
*C08G 18/75* (2006.01)
*C08K 5/17* (2006.01)
*A61L 15/26* (2006.01)
*A61L 15/58* (2006.01)
*A61L 24/04* (2006.01)

(52) U.S. Cl.
CPC .......... *C08K 5/17* (2013.01); *A61L 15/26* (2013.01); *A61L 15/58* (2013.01); *A61L 24/046* (2013.01); *C08L 2201/54* (2013.01); *C08L 2203/02* (2013.01)

(58) Field of Classification Search
CPC ............ C08G 18/4009; C08G 18/3228; C08G 18/4808; C08G 18/4804; C08G 18/4825; C08G 18/4829; C08G 18/4833; C08G 18/4837; C08G 18/4841; C08G 18/4845; C08G 18/4858; C08G 18/4854; C08G 18/72; C08G 18/721; C08G 18/722; C08G 18/725; C08G 18/73; C08G 18/735; C08G 18/755; B05D 3/02; B05D 3/0209; B05D 3/0218; B05D 3/0227; B05D 3/0236; B05D 3/0245; B05D 3/0254; B05D 3/0263; B05D 3/0272; B05D 3/0281; B05D 3/029; A61L 24/00; A61L 24/04; A61L 24/043; A61L 24/046
See application file for complete search history.

(56) References Cited

U.S. PATENT DOCUMENTS 6,156,424 A 12/2000 Taylor
2012/0121902 A1* 5/2012 Dorr ................... C09D 175/08
428/375

FOREIGN PATENT DOCUMENTS

| WO | WO-0162818 A1 | 8/2001 | |
|---|---|---|---|
| WO | WO-2010142393 A1 * | 12/2010 | ........... C08G 18/722 |
| WO | WO-2013136108 A1 | 9/2013 | |

* cited by examiner

CONTACT ADHESIVE PRODUCT BASED ON POLYURETHANE RESIN, PRODUCTION THEREOF, AND CORRESPONDING CONTACT ADHESIVE

CROSS-REFERENCE TO RELATED APPLICATIONS

This application is a national stage application (under 35 U.S.C. § 371) of PCT/EP2017/066197, filed Jun. 29, 2017, which claims benefit of European Application No. 16177190.2, filed Jun. 30, 2016, both of which are incorporated herein by reference in their entirety.

The present invention relates to a contact-adhesive product comprising a substrate and to a specific polyurethaneurea, and to a process for producing the contact-adhesive product. The invention likewise provides a specific polyurethaneurea and a contact adhesive comprising said polyurethaneurea.

Contact adhesives are used in many applications, especially medical applications, for example bandages for compression treatment. What is important here is that adhesives that enable storage of the products on rolls inter alia without such strong bonding of the individual layers that they can be unwound from the roll only with considerable expenditure of force, if at all, are used. At the same time, however, the layers, when used on the human body, should have good adhesion to one another only by virtue of gentle pressure or tensile stress, but without the action of heat, radiation or similar external effects, and reliably seal the bandage, but not stick to the skin, hair or clothing, and also be reversibly detachable and, in the ideal case, even be reusable repeatedly with the same adhesive properties.

Latex formulations based on natural rubbers are often used as adhesive components in such products. However, this entails disadvantages such as discoloration on aging, often an unpleasant odor and also not uncommonly allergic reactions of the skin.

For instance, U.S. Pat. No. 6,156,424 describes, inter alia, contact-adhesive products for use in bandages or dressings, based on substrates impregnated with water-based polymers. The polymers used are inherently crystalline elastomeric polymers such as polychloroprenes, but also polyesterpolyurethanes or polycaprolactoneurethanes. A disadvantage here is that these are usable only in combination with particular tackifiers. It is always necessary to avoid complete crystallization of the products since they otherwise lose their tack. This is difficult to ensure particularly in the case of storage for a long period.

U.S. Pat. No. 5,692,937 describes contact adhesives that are suitable for extensible products such as bandages and are based on aqueous dispersions of polyesterpolyurethanes. However, the products described therein have low contact tack which is insufficient on its own for many applications, and are therefore preferably used in combination with other adhesive dispersions based on polyacrylates, which are not very desirable. Furthermore, the dispersions and the adhesive films formed therefrom have a yellow-brown color which is not very suitable as contact adhesive for medical products since it gives rise to an unhygienic and dirty appearance of the product.

CN104725589 A also already describes the use of aqueous polyurethane dispersions for self adhesive elastic bandages. However, the bandages described therein likewise have insufficient contact tack.

It was an object of the present invention at least to partly overcome at least one disadvantage of the prior art.

A further object of the present invention was that of providing a contact-adhesive product that on the one hand can be stored on rolls without strong bonding of the individual layers, but the layers on the other hand, when used on the human body, have good bonding to one another without action of heat or the like.

It was a further object of the present invention to provide a contact-adhesive product that has high colorfastness, especially high light stability.

At least one of these objects was surprisingly achieved by the provision of a contact-adhesive product comprising a substrate and a polyurethaneurea, obtainable by reacting at least A) one aliphatic polyisocyanate component having an average isocyanate functionality of ≥1.8 and ≤2.6,
B) one polymeric polyetherpolyol component.
C) one amino-functional chain extender component having at least 2 isocyanate-reactive amino groups, containing at least one amino-functional compound C1) that does not have any ionic or ionogenic groups and/or an amino-functional compound C2) that has ionic or ionogenic groups,
D) optionally further hydrophilizing components different than C2),
E) optionally hydroxy-functional compounds having a molecular weight of 62 to 399 mol/g,
F) optionally further polymeric polyols different than B),
G) one compound having exactly one isocyanate-reactive group or one compound having more than one isocyanate-reactive group, where only one of the isocyanate-reactive groups reacts with the isocyanate groups present in the reaction mixture under the reaction conditions chosen, and
H) optionally one aliphatic polyisocyanate component having an average isocyanate functionality of ≥2.6 and ≤4, wherein components B) and F) together contain <30% by weight of component F), based on the total mass of components B) and F).

It has been found that, surprisingly, based on the specific polyurethaneureas mentioned, it was possible to obtain contact-adhesive products that on the one hand can be stored on rolls without strong bonding of the individual layers, but the layers on the other hand, when used on the human body, have good bonding to one another without action of heat or the like.

"Contact-adhesive" in the context of this invention means that an individual layer of the material in question (contact adhesive) or the product per se has only very low tack, if any. Only contact and preferably pressing with a second layer of the same material or product gives rise to a bond of the two material layers with a good bonding force. The contact adhesive consequently has to be applied to both parts or layers to be bonded and is then preferably dried until there is no longer any perceptible tack.

Polyurethaneureas in the context of the invention are polymeric compounds having at least two, preferably at least three, urethane-containing repeat units:

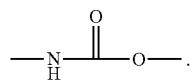

According to the invention, the polyurethaneureas, by virtue of their preparation, also have repeat units that contain urea groups

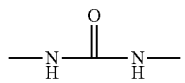

as formed particularly in the reaction of isocyanate-terminated prepolymers with amino-functional compounds.

Ionogenic groups in the context of this invention are understood to mean those functional groups that are capable of forming ionic groups, for example by neutralization with a base.

Component A) may be any polyisocyanate that the person skilled in the art would use for the purpose. Polyisocyanates suitable with preference as component A) are especially the aliphatic polyisocyanates known per se to the person skilled in the art that have an average isocyanate functionality of ≥1.8 and ≤2.6. The term "aliphatic" also includes cycloaliphatic and/or araliphatic polyisocyanates.

Mean isocyanate functionality is understood to mean the average number of isocyanate groups per molecule.

Preferred polyisocyanates are those in the molecular weight range from 140 to 336 g/mol. These are more preferably selected from the group consisting of 1,4-diisocyanatobutane (BDI), pentane 1,5-diisocyanate (PDI) 1,6-diisocyanatohexane (HDI), 1,3-bis(isocyanatomethyl)benzene (xylylene 1,3-diisocyanate, XDI), 1,4-bis(isocyanatomethyl)benzene (xylylene 1,4-diisocyanate, XDI), 1,3-bis(1-isocyanato-1-methylethyl)benzene (TMXDI), 1,4-bis(1-isocyanato-1-methylethyl)benzene (TMXDI), 4-isocyanatomethyloctane 1,8-diisocyanate (trisisocyanatononane (TIN)), 2-methyl-1,5-diisocyanatopentane, 1,5-diisocyanato-2,2-dimethylpentane, 2,2,4- or 2,4,4-trimethyl1,6-diisocyanatohexane, 1,10-diisocyanatodecane, and the cycloaliphatic diisocyanates 1,3- or 1,4-diisocyanatocyclohexane, 1,4-diisocyanato-3,3,5-trimethylcyclohexane, 1,3-diisocyanato-2(4)-methylcyclohexane, 1-isocyanato-3,3,5-trimethyl-5-isocyanatomethylcyclohexane (isophorone diisocyanate, IPDI), 1-isocyanato-1-methyl-4(3)isocyanatomethylcyclohexane, 1,8-diisocyanato-p-methane, 4,4'-diisocyanato-1,1'-bi(cyclohexyl), 4,4'-diisocyanato-3,3'-dimethyl-1,1)-bi(cyclohexyl), 4,4'-diisocyanato-2, 2',5,5'-tetramethyl-1,1'-bi(cyclohexyl), 4,4'- and/or 2,4'-diisocyanatodicyclohexylmethane, 4,4'-diisocyanato-3,3'-dimethyldicyclohexylmethane, 4,4'-diisocyanato-3,3',5,5'-tetramethyldicyclohexylmethane, 1,3-diisocyanatoadamantane, and 1,3-dimethyl-5,7-diisocyanatoadamantane or any mixtures of such isocyanates. The polyisocyanates are most preferably selected from butylene 1,4-diisocyanate, pentamethylene 1,5-diisocyanate (PDI), hexamethylene 1,6-diisocyanate (HDI), isophorone diisocyanate (IPDI), 2,2,4- and/or 2,4,4-trimethythexamethylene diisocyanate, the isomeric bis(4,4'-isocyanatocyclohexyl)methanes or mixtures thereof with any isomer content (H12-MDI), cyclohexylene 1,4-diisocyanate, 4-isocyanatomethyloctane 1,8-diisocyanate (nonan triisocyanate) and alkyl 2,6-diisocyanatohexanoates (lysine diisocyanates) having C1-C8-alkyl groups.

As well as the aforementioned polyisocyanates, it is also possible to use modified diisocyanates having a mean isocyanate functionality ≥2 and ≤2.6, with uretdione, isocyanurate, urethane, allophanate, biuret, iminooxadiazinedione or oxadiazinetrione structure, and mixtures of proportions of these and/or the above.

Preference is given to polyisocyanates or polyisocyanate mixtures of the aforementioned type having exclusively aliphatically or cycloaliphatically bonded isocyanate groups or mixtures of these and a mean NCO functionality of the mixture of ≥1.8 and ≤2.6 and more preferably ≥2.0 and ≤2.4.

More preferably, the organic polyisocyanate component A) contains an aliphatic or cycloaliphatic polyisocyanate selected from HDI, IPDI and/or H12-MDI or the modification products thereof, most preferably selected from HDI and/or IPDI.

In an especially preferred variant, IPDI and HDI are present in a mixture as component A).

The weight ratio of IPDI:HDI here is preferably in the range from 1.05 to 10, more preferably in the range from 1.1 to 5, and most preferably in the range from 1.1 to 1.5.

In a preferred embodiment, the polyurethaneurea used in accordance with the invention is prepared using ≥5% and ≤40% by weight of component A) and more preferably ≥10% and ≤35% by weight of component A), based in each case on the total mass of the polyurethaneurea.

In a further preferred embodiment, the polyurethaneurea is also prepared using component H), an aliphatic polyisocyanate component having a mean isocyanate functionality (mean number of isocyanate groups per molecule) of >2.6 and ≤4, preferably ≥2.8 and ≤3.8. Component H) is preferably used in a mixture with component A).

Particularly suitable components H) are oligomeric diisocyanates having a functionality of >2.6 and ≤4, preferably ≥2.8 and ≤3.8, having isocyanurate, urethane, allophanate, biuret, iminooxadiazinedione or oxadiazinetrione structure. Most preferably, H) contains isocyanurate structures.

More preferably, the organic polyisocyanate component H) consists of an aliphatic or cycloaliphatic polyisocyanate oligomer based on HDI, IPDI and/or H12-MDI, most preferably based on HDI.

The molar ratio of the NCO groups from component A) to component H) is preferably 100:0.5 to 100:50, more preferably 100:2 to 100:15 and most preferably 100:3 to 100:8.

In a preferred embodiment, the polyurethaneurea used in accordance with the invention is prepared using ≥0% and ≤10% by weight of component H) and more preferably ≥0.1% and ≤3% by weight of component H), based in each case on the total mass of the polyurethaneurea.

The polymeric polyetherpolyols used in accordance with the invention as component B) preferably have number-average molecular weights of ≥500 and ≤8000 g/mol, determined via gel permeation chromatography versus polystyrene standard in tetrahydrofuran at 23° C., more preferably ≥400 and ≤6000 g/mol, and especially preferably ≥600 and ≤3000 g/mol, and/or OH functionalities of preferably ≥1.5 and ≤6, more preferably ≥1.8 and ≤3, especially preferably ≥1.9 and ≤2.1.

The expression "polymeric" polyetherpolyols here means more particularly that the polyols mentioned have at least three, more preferably at least four, repeat units bonded to one another.

Number-average molecular weight is determined in the context of this application by gel permeation chromatography (GPC) in tetrahydrofuran at 23° C., unless stated otherwise. The procedure is according to DIN 55672-1: "Gel permeation chromatography, Part 1—Tetrahydrofuran as eluent" (SECurity GPC System from PSS Polymer Service, flow rate 1.0 ml/min; columns: 2×PSS SDV linear M, 8×300 mm, 5 μm; RID detector). Polystyrene samples of known molar mass are used for calibration. The number-average molecular weight is calculated with software support. Baseline points and evaluation limits are fixed according to DIN 55672 Part 1.

Suitable polyetherpolyols are, for example, the addition products, known per se, of styrene oxide, ethylene oxide, propylene oxide, butylene oxide and/or epichlorohydrin onto di- or polyfunctional starter molecules. Polyalkylene glycols in particular, such as polyethylene glycols, polypropylene glycols and/or polybutylene glycols, are applicable, especially with the abovementioned preferred molecular weights. Suitable starter molecules used may be all compounds known according to prior art, for example water, butyldiglycol, glycerol, diethylene glycol, trimethylolpropane, propylene glycol, sorbitol, ethylenediamine, triethanolamine, butane-1,4-diol.

In a preferred embodiment of the product, component B) contains or consists of poly(tetramethylene glycol) polyetherpolyols (such as (HO—(CH$_2$—CH$_2$—CH$_2$—CH$_2$—O)$_x$—H).

Suitable poly(tetramethylene glycol) polyetherpolyols are obtainable, for example, by polymerization of tetrahydrofuran by means of cationic ring opening.

In a further preferred embodiment of the product, component B) contains or consists of a mixture of poly(tetramethylene glycol) polyetherpolyols, where the poly(tetramethylene glycol) polyetherpolyols differ in their number-average molecular weights.

In a particularly preferred embodiment, component B) contains a mixture of poly(tetramethylene glycol) polyetherpolyols I having a number-average molecular weight $M_n$ within a range from ≥400 and ≤1500 g/mol, more preferably within a range from ≥600 and ≤1200 g/mol, most preferably within a range of 1000 g/mol, and poly(tetramethylene glycol) polyetherpolyols II having a number-average molecular weight $M_n$ within a range from ≥1500 and ≤8000 g/mol, more preferably within a range from ≥1800 and ≤3000 g/mol, most preferably of 2000 g/mol.

The weight ratio of the poly(tetramethylene glycol) polyetherpolyols I to the poly(tetramethylene glycol) polyetherpolyols II is preferably in the range from 0.1 to 10, more preferably in the range from 0.2 to 10, most preferably in the range from 1 to 6.

According to the invention, the polyurethaneurea is prepared using an amino-functional chain extender component C) having at least 2 isocyanate-reactive amino groups, containing at least one amino-functional compound C1) that does not have any ionic or ionogenic groups and/or an amino-functional compound C2) that has ionic or ionogenic groups.

The amino-functional compounds of component C) component are preferably selected from primary and/or secondary diamines. More particularly, the amino-functional compounds C) comprise at least one diamine.

In a preferred embodiment of the product, the amino-functional component C) comprises at least one amino-functional compound C2) having ionic and/or ionogenic groups.

In a further preferred embodiment of the invention, the amino-functional component C) comprises both amino-functional compounds C2) having ionic and/or ionogenic groups and amino-functional compounds C1) having no ionic or ionogenic group.

For example, components C1) used may be organic di- or polyamines, for example ethylene-1,2-diamine, 1,2- and 1,3-diaminopropane, 1,4-diaminobutane, 1,6-diaminonexane, isophoronediamine (IPDA), isomer mixture of 2,2,4- and 2,4,4-trimethylhexamethylenediamine, 2-methylpentamethylenediamine, diethylenetriamine, 4,4-diaminodicyclohexylmethane and/or dimethylethylenediamine or mixtures of at least two of these.

Preferably, component-C1) is selected from the group consisting of ethylene-1,2-diamine, bis(4-aminocyclohexyl)methane, 1,4-diaminobutane, IPDA, ethanolamine, diethanolamine and diethylenetriamine or a mixture of at least two of these.

In a further preferred embodiment, component C1) contains >75 mol %, more preferably ≥80 mol %, even more preferably ≥85 mol %, further preferably ≥95 mol % and still further preferably 100 mol % of ethylene-1,2-diamine or IPDA or a mixture of ethylene-1,2-diamine and IPDA, where the sum total of the two amities in relation to the total amount of C1) is preferably within the ranges mentioned. Preferably, component C1) contains >75 mol %, more preferably ≥80 mol %, even more preferably ≥85 mol %, further preferably ≥95 mol % and still further preferably 100 mol % of ethylene-1,2-diamine.

Preferably, the hydrophilizing component C2) comprises at least one anionically hydrophilizing compound. Further preferably, the hydrophilizing component C2) includes an anionically hydrophilizing compound to an extent of at least 80% by weight, or preferably to an extent of at least 90% by weight, based on the total weight of component C2). More preferably, component C2) consists of exclusively anionically hydrophilizing compounds.

Suitable anionically hydrophilizing compounds contain at least one anionic or ionogenic group that can be converted to an anionic group. Further preferably, suitable anionically hydrophilizing compounds have at least two amino groups and more preferably two amino groups. More preferably, the hydrophilizing component C2) comprises or consists of an anionically hydrophilizing compound having at least one anionic or ionogenic group and at least two amino groups.

Suitable anionically hydrophilizing compounds as component C2), also called hydrophilizing agents C2) hereinafter, preferably contain a sulfonic acid or sulfonate group, more preferably a sodium sulfonate group. Suitable anionically hydrophilizing compounds as component C2) are especially the alkali metal salts of the mono- and diaminosulfonic acids. Examples of such anionic hydrophilizing agents are salts of 2-(2-aminoethylamino)ethanesulfonic acid, N-(propyl or butyl)ethylenediaminesulfonic acid or propylene-1,2- or -1,3-diamine-(3-ethylsulfonic acid or mixtures of at least two of these.

Particularly preferred anionic hydrophilizing agents C2) are those that contain sulfonate groups as ionic groups and two amino groups, such as the salts of 2-(2-aminoethylamino)ethylsulfonic acid and propylene-1,3-diamine-β-ethylsulfonic acid. Very particular preference is given to using 2-(2-aminoethylamino)ethylsulfonic acid or salts thereof as anionic hydrophilizing agent C2).

The anionic group in component C2) may optionally also be a carboxylate or carboxylic acid group. In that case, component C2) is preferably selected from diaminocarboxylic acids. In this alternative embodiment, however, the carboxylic acid-based components C2) have to be used in higher concentrations compared to those components (2) bearing sulfonate or sulfonic acid groups. More preferably, therefore, the polyurethaneurea is prepared using no hydrophilizing compounds bearing exclusively carboxylate groups as anionic groups of component C2).

In a preferred embodiment, the polyurethaneurea used in accordance with the invention is prepared using within a range of ≥0.1% and ≤10% by weight of component C2) and more preferably within a range of ≥0.5% and ≤4% by weight of component C2), based in each case on the total mass of the polyurethaneurea.

Hydrophilization can also be accomplished using mixtures of anionic hydrophilizing agents C2) and further hydrophilizing agents D) that are different than C2).

Suitable further hydrophilizing agents D) are, for example, nonionic hydrophilizing compounds D1) and/or hydroxy-functional ionic or ionogenic hydrophilizing agents D2). Preferably, component D) comprises nonionically hydrophilizing components D1).

Suitable hydroxy-functional ionic or ionogenic hydrophilizing agents as component D2) are, for example, hydroxycarboxylic acids such as mono- and dihydroxycarboxylic acids, such as 2-hydroxyacetic acid, 3-hydroxypropanic acid, 12-hydroxy-9-octadecanoic acid (ricinoleic acid), hydroxypivalic acid, lactic acid, dimethylolbutyric acid and/or dimethylolpropionic acid or mixtures of at least two of these. Preference is given to hydroxypivalic acid, lactic acid and/or dimethylolpropionic acid, particular preference to dimethylolpropionic acid. Preference is given to using no hydroxy-functional ionic or ionogenic hydrophilizing agents D2), especially preferably no hydrophilizing agents having carboxylate and hydroxyl groups, for example dimethylolpropionic acid. Preferably, the amount of hydroxy-functional ionic or ionogenic hydrophilizing agents D2) is present in the polyurethaneurea within a range from 0% to 1% by weight, or preferably within a range from 0% to 0.5% by weight, based on the total mass of the polyurethaneurea.

Suitable nonionically hydrophilizing compounds as component D1) are, for example, polyoxyalkylene ethers having isocyanate-reactive groups, such as hydroxyl, amino or thiol groups. Preference is given to monohydroxy-functional polyalkylene oxide polyether alcohols having a statistical average of 5 to 70, preferably 7 to 55, ethylene oxide units per molecule, as obtainable in a manner known per se by alkoxylation of suitable starter molecules (for example in Ullmann Encyclopadie der technischen Chemie [Ullmann's Encyclopedia of Industrial Chemistry], 4th edition, volume 19, Verlag Chemie, Weinheim p. 31-38). These are either pure polyethylene oxide ethers or mixed polyalkylene oxide ethers, where they contain at least 30 mol %, preferably at least 40 mol %, based on all alkylene oxide units present, of ethylene oxide units.

Particularly preferred nonionic compounds are monofunctional mixed polyalkylene oxide polyethers having 40 to 100 mol % of ethylene oxide units and 0 to 60 mol % of propylene oxide units.

Suitable starter molecules for such nonionic hydrophilizing agents are especially saturated monoalcohols such as methanol, ethanol, n-propanol, isopropanol, n-butanol, isobutanol, sec-butanol, the isomeric pentanols, hexanols, octanols and nonanols, n-decanol, n-dodecanol, n-tetradecanol, n-hexadecanol, n-octadecanol, cyclohexanol, the isomeric methylcyclohexanols or hydroxymethylcyclohexane, 3-ethyl-3-hydroxymethyloxetane or tetrahydrofurfuryl alcohol, diethylene glycol monoalkyl ethers, for example diethylene glycol monobutyl ether, unsaturated alcohols such as allyl alcohol, 1,1-dimethylallyl alcohol or olein alcohol, aromatic alcohols such as phenol, the isomeric cresols or methoxyphenols, araliphatic alcohols such as benzyl alcohol, anisyl alcohol or cinnamyl alcohol, secondary monoamines such as dimethylamine, diethylamine, dipropylamine, diisopropylamine, dibutylamine, bis(2-ethylhexyl) amine, N-methyl- and N-ethylcyclohexylamine or dicyclohexylamine, and heterocyclic secondary amines such as morpholine, pyrrolidine, piperidine or 1H-pyrazole. Preferred starter molecules are saturated monoalcohols of the aforementioned type. Particular preference is given to using diethylene glycol monobutyl ether, methanol or n-butanol as starter molecules.

Alkylene oxides suitable for the alkoxylation reaction are especially ethylene oxide and propylene oxide, which can be used in the alkoxylation reaction in any sequence or else in a mixture.

In a preferred embodiment of the invention, the polyurethaneurea used in accordance with the invention contains within a range of ≥0% and ≤20% by weight of component D), preferably within a range of ≥0% and ≤10% by weight of component D) and most preferably within a range of ≥0% and ≤5% by weight of component D), based in each case on the total mass of the polyurethaneurea. In a further preferred embodiment, component D) is not used for preparation of the polyurethaneurea.

As component E) it is optionally possible to use polyols, especially nonpolymeric polyols, of said molecular weight range from 62 to 399 mol/g having up to 20 carbon atoms, such as ethylene glycol, diethylene glycol, triethylene glycol, propane-1,2-diol, propane-1,3-diol, butane-1,4-diol, 1,3-butylene glycol, cyclohexanediol, cyclohexane-1,4-dimethanol, hexane-1,6-diol, neopentyl glycol, hydroquinone dihydroxyethyl ether, bisphenol A (2,2-bis(4-hydroxyphenyl)propane), hydrogenated bisphenol A (2,2-bis(4-hydroxycyclohexyl)propane), trimethylolpropane, trimethylolethane, glycerol, pentaerythritol and any desired mixtures thereof with one another.

In a preferred embodiment of the invention, the polyurethaneurea used in accordance with the invention contains ≤10% by weight of component E), preferably ≤5% by weight and more preferably 0% by weight of component E), based in each case on the total mass of the polyurethaneurea. Preferably, the polyurethaneurea includes component E) within a range from 0.1% to 10% by weight, preferably within a range from 0.2% to 8% by weight, preferably within a range from 0.1% to 5% by weight, based in each case on the total mass of the polyurethaneurea. In a further preferred embodiment, component E) is not used for preparation of the polyurethaneurea.

In a preferred embodiment, the polyurethaneurea used in accordance with the invention is prepared using within a range of ≥0.5% and ≤20% by weight of the sum total of components C1) and any E) and more preferably within a range of ≥1% and ≤15% by weight of the sum total of components C1) and any E), based in each case on the total mass of the polyurethaneurea.

As component F) it is possible to use further polymeric polyols that are different than B).

Preference is given to polymeric polyols not covered by the definition of B) because they are not polyetherpolyols—for example the following polyols that are known per se in polyurethane coating technology: polyesterpolyols, polyacrylatepolyols, polyurethanepolyols, polycarbonatepolyols, polyesterpolyacrylatepolyols, polyurethanepolyacrylatepolyols, poly urethanepolyesterpolyols, polyurethanepolycarbonatepolyols and polyesterpolycarbonatepolyols.

Preferably, component F) does not comprise polymeric polyols having ester groups, especially not polyesterpolyols.

According to the invention, components B) and F) together contain ≤30% by weight, preferably ≤10% by weight and more preferably ≤5% by weight of component F), based on the total mass of components B) and F). Most preferably, component F) is not used for preparation of the polyurethaneurea.

In a preferred embodiment, the polyurethaneurea used in accordance with the invention is prepared using within a range of ≥55% and ≤90% by weight of the sum total of components B) and any F) and more preferably within a range of ≥60% and ≤85% by weight of the sum total of components B) and any F), based in each case on the total mass of the polyurethaneurea.

Component G) comprises compounds having exactly one isocyanate-reactive group or compounds having more than one isocyanate-reactive group, where only one of the isocyanate-reactive groups reacts with the isocyanate groups present in the reaction mixture under the reaction conditions chosen.

The isocyanate-reactive groups of component G) may be any functional group that can react with an isocyanate group, for example hydroxyl groups, thiol groups or primary and secondary amino groups.

Isocyanate-reactive groups in the context of the invention are especially preferably primary or secondary amino groups that react with isocyanate groups to form urea groups. As well as the amino group, the compounds of component G) may also have other groups that are isocyanate-reactive in principle, such as OH groups, where just one of the isocyanate-reactive groups reacts with the isocyanate groups present in the reaction mixture under the reaction conditions chosen. This can be effected, for example, by reaction of appropriate amino alcohols at relatively low temperatures, for example at 0 to 60° C., preferably at 20 to 40° C. Preference is given here to working in the absence of catalysts that would catalyze the reaction of isocyanate groups with alcohol groups.

Examples of suitable compounds of component G) are primary/secondary amines, such as methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine, diethanolamine, 3-amino-1-methylaminopropane, 3-amino-1-ethylaminopropane, 3-amino-1-cyclohexylaminopropane, 3-amino-1-methylaminobutane, ethanolamine, 3-aminopropanol or neopentanolamine.

Suitable monofunctional compounds are also ethanol, n-butanol, ethylene glycol monobutyl ether, diethylene glycol monomethyl ether, diethylene glycol monobutyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, tripropylene glycol monobutyl ether, 2-ethyl hexanol, 1-octanol, 1-dodecanol, 1-hexadecanol.

In a preferred embodiment, the polyurethaneurea used in accordance with the invention is prepared using ≥0.1% and ≤20% by weight of component G) and more preferably ≥0.3% and ≤10% by weight of component G), based in each case on the total mass of the polyurethaneurea.

In a particularly preferred embodiment of the invention, component H) is used and the molar ratio of component G) to component H) is preferably 5:1 to 1:5, more preferably 1.5:1 to 1:4 and most preferably 1:1 to 1:3.

In a preferred embodiment, the polyurethaneureas used in accordance with the invention are prepared using components A) to H) in the following amounts, where the individual amounts always add up to 100% by weight:

5% to 40% by weight of component A),
55% to 90% by weight of the sum total of components B) and optionally F),
0.5% to 20% by weight of the sum total of components C1) and optionally E),
0.1% to 10% by weight of component C2),
0% to 20% by weight of component D),
0.1% to 20% by weight of component G) and
0% to 10% by weight of component H).

In a particularly preferred embodiment, the polyurethaneureas used in accordance with the invention are prepared using components A) to H) in the following amounts, where the individual amounts always add up to 100% by weight:

10% to 35% by weight of component A),
60% to 85% by weight of the sum total of components B) and optionally F),
1% to 15% by weight of the sum total of components C1) and optionally E),
0.5% to 4% by weight of component C2),
0% to 10% by weight of component D),
0.3% to 10% by weight of component G) and
0.1% to 3% by weight of component H).

In a preferred embodiment of the invention, the contact-adhesive product comprises a polyurethaneurea obtainable by reaction of at least A) one aliphatic polyisocyanate component having an average isocyanate functionality of ≥1.8 and ≤2.6, selected from HDI, IPDI and/or H12-MDI or modification products thereof,
B) one polymeric polyetherpolyol component, consisting of poly(tetramethylene glycol) polyetherpolyols (such as (HO—CH$_2$—CH$_2$—CH$_2$—CH$_2$—O)$_x$—H),
C) one amino-functional chain extender component having at least 2 isocyanate-reactive primary and/or secondary amino groups, containing at least one amino-functional compound C1) that does not have any ionic or ionogenic groups and/or an amino-functional compound C2) that has ionic or ionogenic groups,
D) optionally further hydrophilizing components different than C2),
E) optionally hydroxy-functional compounds having a molecular weight of 62 to 399 mol/g,
F) optionally further polymeric polyols different than B),
G) one compound having exactly one isocyanate-reactive group or one compound having more than one isocyanate-reactive group, where only one of the isocyanate-reactive groups reacts with the isocyanate groups present in the reaction mixture under the reaction conditions chosen, and
H) optionally one aliphatic polyisocyanate component having an average isocyanate functionality of >2.6 and ≤4, where component H) consists of an aliphatic or cycloaliphatic polyisocyanate oligomer having isocyanurate, urethane, allophanate, biuret, iminooxadiazindione or oxadiazinetrione structure, wherein components B) and F) together contain ≤30% by weight of component F), based on the total mass of components B) and F).

In a particularly preferred embodiment of the invention, the contact-adhesive product comprises a polyurethaneurea obtainable by reaction of at least A) one aliphatic polyisocyanate component which is a mixture of IPDI and HDI,
B) one polymeric polyetherpolyol component which is a mixture of at least two poly(tetramethylene glycol) polyetherpolyols and where the poly(tetramethylene glycol) polyetherpolyols differ in their number-average molecular weights, C) one amino-functional chain extender component having 2 isocyanate-reactive primary and/or secondary amino groups, containing at least one amino-functional compound C1) that does not have any ionic or ionogenic groups and/or an amino-functional compound C2) that has ionic or ionogenic groups, D) optionally further hydrophilizing components that are different than C2), which are nonionically hydrophilizing components D1), E) optionally hydroxy-functional compounds having a molecular weight of 62 to 399 mol/g, F) optionally further polymeric polyols that are different than B), G) one compound having exactly one isocyanate-reactive group or one compound having more than one isocyanate-reactive group, where only one of the isocyanate-reactive groups reacts with the isocyanate groups present in the reaction mixture under the reaction conditions chosen, where the isocyanate-reactive group is a primary and/or secondary amino and/or hydroxyl group, and H) optionally one aliphatic polyisocyanate component having an average isocyanate functionality of >2.6 and ≤4, where component H) consists of an aliphatic or cycloaliphatic polyisocyanate oligomer having isocyanurate, urethane, allophanate, biuret, iminooxadiazinedione or oxadiazinetrione structure, based on HDI, IPDI and/or H12-MDI, wherein components B) and F) together contain ≤30% by weight of component F), based on the total mass of components B) and F).

Most preferably, the polyurethaneurea used in accordance with the invention is obtainable by reacting exclusively components A) to H). In that case, no further components are used for preparation of the polyurethaneurea.

The number-average molecular weight of the polyurethaneureas used with preference in accordance with the invention is preferably from ≥2000 to ≤300 000 g/mol, preferably from ≥5000 to ≤150 000 g/mol.

The polyurethaneurea used in accordance with the invention is preferably amorphous and has a Tg≤25° C., more preferably of ≤−50° C. and most preferably of ≤−70° C.

"Amorphous" in the context of this invention means that the polyurethaneurea, within the temperature range specified in the test method detailed hereinafter, forms only such minor crystalline components, if any, that, by means of the DSC measurements described, it is possible to find only one or more glass transition points $T_g$ but no fusion regions having an enthalpy of fusion ≥20 J/g within the temperature range mentioned.

The glass transition temperature $T_g$ is determined in the context of this invention by means of dynamic differential calorimetry in accordance with DIN EN 61006, Method A, using a DSC instrument calibrated with indium and lead for determination of $T_g$, by conducting three directly consecutive runs composed of a heating operation from −100° C. to +150° C., at a heating rate of 20 K/min, with subsequent cooling at a cooling rate of 320 K/min, and using the third heating curve to determine the values and determining $T_g$ as the temperature at half the height of a glass transition step.

If the polyurethaneurea should be in the form of a dispersion, a special procedure is followed in the sample preparation for the DSC measurements. In the determination of the glass transition temperature $T_g$ of dispersions by means of DSC, the $T_g$ of the polymer can be masked by the caloric effects of the dispersant (water, neutralizing agent, emulsifier, cosolvent etc.) or distinctly lowered owing to miscibility with the polymer. Therefore, the dispersant, prior to the DSC measurement, is preferably first removed completely by suitable drying, since even small residual amounts of dispersant act as plasticizer and can lower the glass transition temperature as a result. The dispersion is therefore preferably knife-coated onto a glass plate at wet film thickness (WFT) 100 µm, flashed off and then dried gently in a dry box at RT and 0% relative air humidity (rh) for two days. After this sample preparation can in the first heating operation of the DSC measurement still a broad endothermic evaporation range of residual moisture in the film. In order to keep the particular values free of such influences as far as possible, the third heating curve is therefore evaluated.

The polyurethaneurea used in accordance with the invention for production of the product is preferably in a physiologically acceptable medium. The medium is more preferably water, and the polyurethaneurea is most preferably in the form of an aqueous dispersion. In general, alongside other liquid media that are optionally present, for example solvents, water generally forms the main constituent (>50% by weight) of the dispersion medium, based on the total amount of the liquid dispersion medium, and possibly even the sole liquid dispersion medium.

The product of the invention itself contains the polyurethaneurea per se, which contains only residual amounts of this medium, if any.

Preferably, the polyurethaneurea used is therefore dispersible in water, which means in the context of this invention that the polyurethaneurea at 23° C. can form a sedimentation-stable dispersion in water, especially deionized water.

The polyurethaneureas used in accordance with the invention are preferably obtainable by preparing isocyanate-functional polyurethane prepolymers a) from components A), B) and optionally D) and/or C2), and optionally compounds E) and/or H) (step a), and the free NCO groups thereof are then wholly or partially reacted with the amino-functional chain-extender component C), and also component G) and optionally components D) and H) (step b)).

But when component H) is not used until step b), it is preferably added prior to the addition of component C) and reacted with the prepolymer a).

In a preferred embodiment of the invention, in step b), reaction is effected with a diamine or multiple diamines (component C) with chain extension, also with addition of the monofunctional component G) as chain terminator to control the molecular weight.

Components A) to H) are defined here as specified above. The abovementioned preferred embodiments are also applicable.

Preferably, in step b), the reaction of the prepolymer a) for preparation of the polyurethaneurea, a mixture of components C1), C2) and G) is reacted. The use of component C1) can result in formation of a high molar mass without a rise in the viscosity of the isocyanate-functional prepolymer prepared beforehand to a degree that would be a barrier to processing. The use of the combination of components C1), C2) and G) can establish an optimal balance between hydrophilicity and chain length.

Preferably, the polyurethane prepolymer a) used in accordance with the invention has terminal isocyanate groups, meaning that the isocyanate groups are at the chain ends of the prepolymer. More preferably, all chain ends of the prepolymer have isocyanate groups.

The hydrophilizing components C2) and/or D) can be used to control the hydrophilicity of the prepolymer. In addition, further components are of course also significant for the hydrophilicity of the prepolymer, especially also the hydrophilicity of component B).

Preferably, the isocyanate-functional polyurethane prepolymers a) are water-insoluble and non-water-dispersible.

In the context of the invention, the term "water-insoluble, non-water-dispersible polyurethane prepolymer" means more particularly that the water solubility of the prepolymer used in accordance with the invention at 23° C. is less than 10 g/liter, preferably less than 5 g/liter, and the prepolymer at 23° does not result in any sedimentation-stable dispersion in water, especially deionized water. In other words, the prepolymer settles out when an attempt is made to disperse it in water. The water insolubility or lack of dispersibility in water relates to deionized water without addition of surfactants.

Moreover, the polyurethane prepolymer A) used in accordance with the invention preferably has essentially neither ionic groups nor ionogenic groups (groups capable of forming ionic groups). In the context of the present invention, this means that the proportion of the ionic and/or ionogenic groups, such as anionic groups in particular, such as carboxylate or sulfate, or of cationic groups is less than 15 milliequivalents per 100 g of polyurethane prepolymer a1), preferably less than 5 milliequivalents, more preferably less than 1 milliequivalent and most preferably less than 0.1 milliequivalent per 100 g of polyurethane prepolymer a).

In the case of acidic ionic and/or ionogenic groups, the acid number of the prepolymer is appropriately below 30 mg KOH/g of prepolymer, preferably below 10 mg KOH/g of prepolymer. The acid number indicates the mass of potassium hydroxide in milligrams required to neutralize 1 g of the sample to be examined (measurement to DIN EN ISO 211). The neutralized acids, i.e. the corresponding salts, naturally have a zero or reduced acid number. What is crucial here in accordance with the invention is the acid number of the corresponding free acid.

The water-insoluble, non-water-dispersible isocyanate-functional polyurethane prepolymers a) here are preferably obtainable exclusively from components A), B) and optionally D), E) and/or H).

The components are defined here as specified above. The abovementioned preferred embodiments are also applicable.

Consequently, in this embodiment, preference is given to using no ionically hydrophilizing components C2) or else D2) for preparation of the prepolymer a). Nor is component G) added in this step. The hydrophilizing agents D1) are preferably used in such amounts that the prepolymer is nevertheless water-insoluble and non-water-dispersible. More preferably ≤10% by weight of component D1), even more preferably 5% by weight and further preferably ≤2% by weight of component D1) is used, based in each case on the total mass of the polyurethaneurea. Further preferably, component D1) is not used for preparation of the prepolymer a).

For this embodiment of the invention, component B) has neither ionic nor ionogenic groups. In addition, in this embodiment of the invention, preference is given to using, as component B), polyetherpolyols only, especially polyalkylene oxide ethers containing ≤10 mol % and, based on all alkylene oxide units present, of ethylene oxide units and preferably no ethylene oxide units.

The polyurethaneureas used with preference in this embodiment of the invention consequently have ionic or ionogenic groups, preferably anionic groups; these anionic groups are introduced into the polyurethaneureas used in accordance with the invention via the hydrophilizing component C2) used in step b). The polyurethaneureas used in accordance with the invention optionally additionally include nonionic components for hydrophilization.

More preferably, the polyurethaneureas used in accordance with the invention, for hydrophilization, contain exclusively sulfonate groups that are introduced into the polyurethaneurea in step b) via corresponding diamines as component C2).

In an alternative, less preferred embodiment of the invention, the prepolymers a) used for preparation of the polyurethaneurea of the invention are water-soluble or water-dispersible. In this embodiment, the hydrophilizing components D) and/or C2) are used in the preparation of the prepolymer a) in an amount sufficient for the prepolymer to be water-soluble or water-dispersible. The prepolymer a) here preferably has ionic or ionogenic groups.

Suitable hydrophilizing components D) and C2) for this embodiment of the invention are the compounds mentioned above for D) and C2). The hydrophilizing components used are preferably at least the compounds mentioned above under D1) and/or C2).

The polyurethaneureas used for preparation of the products of the invention are preferably dispersed in water before, during or after step b), more preferably during or after step b). In this way, a dispersion of the polyurethaneureas is obtained.

The production of the polyurethaneurea dispersions can be conducted here in one or more stage(s) in a homogeneous reaction or in a multistage reaction, partly in disperse phase. Preparation of the prepolymer a) is preferably followed by a dispersion, emulsification or dissolution step. This is optionally followed by a further polyaddition or modification in disperse phase. In this case, the solvent or dispersant suitable for the corresponding prepolymer in each case, for example water or acetone or mixtures thereof, is chosen.

It is possible here to use any methods known from the prior art, for example prepolymer mixing methods, acetone methods or melt dispersion methods. Preference is given to employing the acetone method.

For preparation by the acetone method, it is customary to wholly or partly initially charge constituents B), optionally D) and E) and the polyisocyanate component A), optionally in combination with component H) for preparation of an isocyanate-functional polyurethane prepolymer, and optionally to dilute them with a solvent which is water-miscible but inert toward isocyanate groups, and to heat them to temperatures in the range from 50 to 120° C., The isocyanate addition reaction can be accelerated using the catalysts known in polyurethane chemistry.

Suitable solvents are the customary aliphatic keto-functional solvents, such as acetone, 2-butanone, which can be added not just at the start of the preparation but optionally also in portions at a later stage. Preference is given to acetone and 2-butanone, particular preference to acetone. The addition of other solvents without isocyanate-reactive groups is also possible, but not preferred.

Subsequently, any constituents of A), B) and optionally H), D) and E) which have not yet been added at the start of the reaction can be metered in.

In the preparation of the polyurethane prepolymers from A), B) and optionally H), D) and E), the molar ratio of isocyanate groups to isocyanate reactive groups is preferably 1.05 to 3.5, more preferably 1.1 to 3.0 and most preferably 1.1 to 2.5.

The conversion of components A), B) and optionally H), D) and, E) to the prepolymer can be effected in part or in fill, but preferably in full. In this way, polyurethane prepolymers containing free isocyanate groups can be obtained in neat form or in solution.

If ionogenic groups, for example carboxyl groups, should be present in the prepolymer, these can be converted to ionic groups by neutralization in a further step.

In the neutralization step, for partial or complete conversion of potentially anionic groups to anionic groups, it is possible to use bases such as tertiary amines, e.g. trialkylamines having 1 to 12 and preferably 1 to 6 carbon atoms, more preferably 2 to 3 carbon atoms, in each alkyl radical, and most preferably alkali metal bases such as the corresponding hydroxides.

Usable neutralizing agents are preferably inorganic bases, such as aqueous ammonia solution or sodium hydroxide or potassium hydroxide; particular preference is given to sodium hydroxide and potassium hydroxide.

The molar amount of the bases is preferably 50 and 125 mol %, more preferably between 70 and 100 mol %, of the molar amount of the acid groups to be neutralized. Neutralization can also be effected simultaneously with the dispersion, in that the dispersion water already contains the neutralizing agent.

After the neutralization, in a further process step, if this has been done only partly, if at all, the prepolymer obtained is dissolved with the aid of aliphatic ketones such as acetone or 2-butanone.

In the chain extension/termination in stage b), components C), G) and optionally D) are reacted with the isocyanate groups still remaining in the prepolymer. Preference is given to conducting the chain extension/termination prior to the dispersion in water.

Suitable components C) for chain extension and G) for chain termination have already been listed above. The abovementioned preferred embodiments are also applicable analogously.

If anionic hydrophilizing agents in accordance with definition C2) having $NH_2$ groups or NH groups are used for chain extension, the chain extension of the prepolymers in step b) is preferably effected prior to the dispersion in water.

The equivalent ratio of NCO-reactive groups in the compounds used for chain extension and chain termination to free NCO groups in the prepolymer is generally between 40% and 150%, preferably between 50% and 110%, more preferably between 60% and 100%.

Components C1), C2) and G) may optionally be used in water- or solvent-diluted form in the process of the invention, individually or in mixtures, any sequence of addition being possible in principle.

When water or organic solvent is included as diluent in step b), the respective diluent content in components C1), C2) and G) used is preferably 40% to 95% by weight.

Dispersion preferably follows after the chain extension and chain termination. For this purpose, the polyurethane polymer that has been dissolved (for example in acetone) and reacted with the amines is either introduced into the dispersion water, optionally under high shear, for example vigorous stirring, or, conversely, the dispersion water is stirred into the chain-extended polyurethane polymer solutions. Preferably, the water is added to the dissolved polyurethane polymer.

The solvent still present in the dispersions after the dispersion step is typically then removed by distillation. Removal even during the dispersion is likewise possible.

The aqueous polyurethaneurea dispersions obtained preferably have a content of volatile organic compounds (VOCs), for example volatile organic solvents, of less than 10% by weight, more preferably of less than 3% by weight, even more preferably of less than 1% by weight, based on the aqueous polyurethaneurea dispersion. VOCs in the context of this invention are especially organic compounds having an initial boiling point of at most 250° C. at a standard pressure of 101.3 kPa.

In the context of the present invention, the content of volatile organic compounds (VOCs) is especially determined by gas chromatography analysis.

The polyurethaneurea is used for preparation of the product preferably as an aqueous dispersion.

The pH of the aqueous polyurethane dispersions used in accordance with the invention is typically less than 9.0, preferably less than 8.5, and is more preferably between 5.5 and 8.0.

In order to achieve good sedimentation stability, the number-average particle size of the specific polyurethaneurea dispersions is preferably less than 750 nm, more preferably less than 500 nm, determined by means of laser correlation spectroscopy after dilution with deionized water (instrument: Malvern Zetasizer 1000. Malvern Inst. Limited).

The solids content of the polyurethaneurea dispersions is preferably 10% to 70% by weight, more preferably 20% to 60% by weight and most preferably 40% to 60% by weight. The solids contents are ascertained by heating a weighed sample to 125° C. to constant weight. At constant weight, the solids content is calculated by reweighing the sample.

Preferably, these polyurethaneurea dispersions include less than 5% by weight, more preferably less than 0.2% by weight, based on the mass of the dispersions, of unbound organic amines.

The polyurethaneurea dispersions used for production of the products of the invention have, at 23° C., at a constant shear rate of $10\ s^{-1}$, preferably a viscosity of $\geq 1$ and $\leq 10\,000$ mPa s, more preferably of $\geq 10$ and $\leq 5000$ mPa s and most preferably of $\geq 100$ and $\leq 4000$ mPa s. The viscosity is determined as described in the Methods section.

In addition, the contact-adhesive product, in accordance with the invention, comprises a substrate.

Substrates used are typically suitable textiles having sufficient elasticity and suitable mechanical properties.

Suitable substrates are preferably textile fabrics. Particular preference is given to fibrous materials having a non-smooth surface as the substrate for the polyurethaneureas used in accordance with the invention. Textile fabrics in the present context of the present invention include, for example, woven fabrics, loop-formed knitted fabrics, braided fabrics, loop-laid fabrics, loop-drawn knitted fabrics, and bonded and unbonded nonwoven fabrics. Preference is given to braided fabrics, especially those composed of warp and weft threads, loop-formed knitted fabrics, especially creped knits, or nonwoven fabrics.

The textile fabrics may be formed from synthetic or natural fibers and/or mixtures thereof. Examples of natural fibers are cellulose, cotton, linen and the chemically modified fibers thereof. Examples of synthetic fibers are polyamide, polyester etc. In principle, textiles made of any fibers are suitable for the process of the invention. Mixtures of different fibers are also suitable. Particular preference is given to the use of a small proportion, especially between 1% and 10% by weight, of an elastic fiber; very particular preference is given here to the use of elastane. By means of the polyurethaneureas used in accordance with the invention, it is possible to treat or upgrade the substrates in all the customary ways, preferably by coating or bonding the fibers to one another or substrates to one another.

Substrates used are preferably products or nonwoven fabrics made of synthetic fibers, cellulose or cotton. Particular preference is given to using nonwoven fabrics, creped knits or braided fabrics based on polyester or polyamide or mixtures thereof with cotton or preferably cellulose fibers that include a proportion of highly elastic fibers of synthetic polymers (e.g. elastane or spandex) of 1% to 10% by weight.

Preferably, these fabrics have basis weights of 20 to 600 gsm (grams per $m^2$ more preferably 25 to 300 gsm and most preferably 28 to 80 gsm.

Substrates are preferably used in the form of continuous tapes, bandages or rolls. Substrates used are preferably elastic tapes having a stretching range from 30% to 500%, more preferably from 60% to 250% and most preferably from 120% to 200%, determined to DIN 53835 Part 2 (Determination of the elastic behavior of textiles by repeated application of tensile load between constant extension limits (total extension)). In addition, the substrates preferably have a maximum tensile force of 100 to 500 N, preferably of 120 to 350 N, determined to DIN EN ISO 13934-1 by means of a tensile strip test.

Very particular preference is given to long-stretch bandages having a stretching range from 120% to 200% and a maximum tensile force of 120 to 350 N. The substrates used preferably have a coarse, rough, incompletely closed surface. This can be defined by the air permeability in the unstretehed state. Air permeahilities of >200 $l/m^2$ s are preferred, more preferably ≥1000 $l/m^2$ and most preferably ≥3000 $l/m^2$ s. The air permeability of the substrates is determined here according to DIN EN ISO 9237.

In a preferred embodiment of the invention, the polyurethaneurea covers at least one face of the substrate at the surface; more preferably, the polyurethaneurea covers two opposite faces of the substrate (front side and reverse side) at the surface. Most preferably, the polyurethaneurea covers the surfaces uniformly.

It is possible here that the substrate is impregnated with the polyurethaneurea across the entire area and thickness, but the coating preferably remains at the surface of the substrate and does not penetrate completely into its interior (bulk) or the fibers themselves.

The contact-adhesive products of the invention are preferably products that are used on the human body. More preferably, the contact-adhesive products are used in medical sectors, such as, more particularly, sports medicine, trauma surgery or orthopedics, both for treatment and for prevention of bone injuries, joint injuries or muscle injuries, or for protection and coverage of the skin or of skin injuries. Further preferred uses are bandages for compression treatment and the fixing of nonadhesive Wound dressings (as secondary dressings).

According to the invention, the contact-adhesive product is preferably a plaster, a dressing, a tape or a bandage, or at least a constituent of these end products.

Tape is understood in the context of this invention to mean especially a plaster adhesive dressing which is used in medical sectors, both for treatment and for prevention of bone injuries, joint injuries or muscle injuries.

The invention further provides a process for producing a contact-adhesive product of the invention, comprising the steps of
I) applying the polyurethaneurea to the substrate in the form of an aqueous polyurethaneurea dispersion and
II) thermally drying the treated substrate at temperatures ≥20° C. and ≤200° C.

For application of the polyurethaneurea in step I, in the form of a polyurethaneurea dispersion, it is preferably blended with admixtures and especially preferably in bubble-free form. The composition formed is referred to hereinafter as polyurethaneurea composition. For production of the contact-adhesive product, preference is given to using a polyurethaneurea composition comprising the polyurethaneurea in the form of an aqueous dispersion and further admixtures.

It is of course possible to adjust the viscosity of the polyurethaneurea dispersion to the required circumstances by dilution or thickening or a combination of both methods in order to achieve desired application thicknesses. It is possible here to use thickeners as admixtures. Typical thickeners are soluble polyacrylate- or polyurethane-based polymers as known from the prior art. Preference is given to thickeners based on polyurethane polymers. The polyurethaneurea dispersion can be diluted using standard solvents, hut preference is given to water.

In addition, admixtures used may be tackifiers in order to adjust the tack of the products. Tackifiers used may be the admixtures known in the prior art. Examples are: water-miscible mono-, di- and multifunctional hydroxyl compounds, preferably aliphatic in nature, for example glycerol, ethylene glycol, propylene glycol, di-, tri- and tetraethyiene glycol, TMP, more preferably glycerol and triethylene glycol, short-chain polyethylene oxides, for example PEG 200, PEG 300, PEG 400, rosin esters, copolymers based on styrene and acrylic esters or phenolic ethers or else mixtures of the aforementioned compounds.

It may also be advantageous to regulate the surface tack, which can lead to blocking of the bandage on the roll, by the addition of fillers as admixtures. These may be: silica gel, silicates, talc, magnesia, calcite, urea and derivatives or other pulverulent solids, especially those that can be incorporated homogeneously into the polyurethaneurea dispersion. In addition, it is also possible to use liquid additives to counter blocking, for example oil-based systems, preferably silicone-containing systems.

Typical further suitable admixtures are surface additives, for example wetting auxiliaries, dyes and/or leveling auxiliaries. The polyurethaneurea composition may also contain all further admixtures known to the person skilled in the art for the respective use.

Application to the substrate in step I) can generally be effected by all known application techniques, specifically by means of a coating bar, dipping bath, squeegee (or roll mill), printing or spray application; preference is given to dipping, spray application and squeegeeing, and particular preference to spray application and squeegeeing.

In the case of application by squeegeeing, the polyurethaneurea composition is preferably applied to the rolls, the separation and contact pressure of which has been optimized for the achievement of the desired layer thickness. Then the textile substrate can be guided through the rolls, with application of the polyurethaneurea composition to the textile to the desired degree. Thus, coating is preferably effected on both sides. It is particularly preferable when application can be effected with one to two squeegee rolls, more preferably in a single pass therethrough.

For coating bar application, the substrate can be fixed beforehand in a clamping apparatus and then the coating bar with the dispersion in front of it can be guided by hand or in an automated manner across the substrate, and the dispersion can be distributed uniformly thereon. Coating can likewise be effected via a typical roll-to-roll coating system with a coating bar, in which the substrate is coated continuously.

In the case of spray application, the substrate is clamped, preferably in a frame, and sprayed with the dispersion on one or both sides from a spray gun. Application can be effected in one or more cross-coating operations, manually or by means of a continuous roll-to-roll spray system.

In the dipping method, the substrate preferably runs through a dispersion bath containing the polyurethaneurea composition and is thereby wetted therewith. The dwell time in the bath, the concentration (or the solids content) of the polyurethaneurea composition and the viscosity thereof can be used to control the layer thicknesses applied. A removal roll or a pair of squeegee rolls can be used to remove excess polyurethaneurea composition. Preference is given here to double-sided coating in a single run.

After application of the polyurethaneurea composition to the substrate, preferably by one of the methods described above, the coating is dried in step ii). The drying is effected by thermal drying, at temperatures between 20° C. and 200° C., preferably between 40° C. and 150° C. and more preferably between 60° C. and 120° C. Thermal drying can be replaced or assisted by IR or microwave drying.

Preferably, in the application of the polyurethaneurea composition to the substrate, at least one face of the substrate is surface-coated; more preferably, two opposite faces of the substrate (front side and reverse side) are surface-coated. Most preferably, coating with the polyurethaneurea composition is effected homogeneously.

Impregnation of the substrate with the polyurea composition is possible across the entire area and thickness. Preferably, however, the polyurethaneurea composition remains at the surface of the substrate and does not penetrate fully into the inner region (bulk) thereof or the fibers themselves.

The invention further provides a poly ethaneurea obtainable by reacting at least
- A) one aliphatic polyisocyanate component having an average isocyanate functionality of ≥1.8 and ≤2.6,
- B) one polymeric polyetherpolyol component,
- C) one amino-functional chain extender component having at least 2 isocyanate-reactive amino groups, containing at least one amino-functional compound C1) that does not have any ionic or ionogenic groups and/or an amino-functional compound C2) that has ionic or ionogenic groups,
- D) optionally further hydrophilizing components different than C2),
- E) optionally hydroxy-functional compounds having a molecular weight of 62 to 399 mol/g,
- F) optionally further polymeric polyols that are different than B),
- G) one compound having exactly one isocyanate-reactive group or one compound having more than one isocyanate-reactive group, where only one of the isocyanate-reactive groups reacts with the isocyanate groups present in the reaction mixture under the reaction conditions chosen, and
- H) one aliphatic polyisocyanate component having an average isocyanate functionality of >2.6 and ≤4, wherein components B) and F) together contain ≤30% by weight of component F), based on the total mass of components B) and F), and components G) and H) are present in a relative molar ratio of 5:1 to 1:5.

In a preferred embodiment of the invention, the molar ratio of component G) to component H) is 5:1 to 1:5, more preferably 1.5:1 to 1:4 and most preferably 1:1 to 1:3.

For components A) to H), the definitions and preferred embodiments mentioned above for the polyurethaneurea present in the product of the invention are applicable analogously.

Especially preferably, component A) is isophorone diisocyanate and/or hexamethylene diisocyanate.

Likewise especially preferably, component B) contains or consists of poly(tetramethylene glycol) polyetherpolyols (such as (HO—(CH$_2$—CH$_2$—CH$_2$—CH$_2$—O)$_x$—H).

Most preferably, component B) contains or consists of a mixture of poly(tetramethylene glycol) polyetherpolyols, where the poly(tetramethylene glycol) polyetherpolyols differ in their number-average molecular weights.

Likewise especially preferably, component C) is at least one amino-functional compound C1) that does not have any ionic or ionogenic groups and an amino-functional compound C2) that has ionic or ionogenic groups contains.

Likewise especially preferably, component D) comprises nonionically hydrophilizing components.

Particularly advantageous embodiments of the invention also result from the combinations of the features that are mentioned hereinabove as being especially preferred.

In a preferred embodiment, the polyurethaneureas used in accordance with the invention are prepared using components A) to H) in the following amounts, where the individual amounts always add up to 100% by weight:
- 5% to 40% by weight of component A),
- 55% to 90% by weight of the sum total of components B) and optionally F),
- 0.5% to 20% by weight of the sum total of components C1) and optionally E),
- 0.1% to 10% by weight of component C2),
- 0% to 20% by weight of component D),
- 0.1% to 20% by weight of component G) and
- 0% to 10% by weight of component H).

In a further preferred embodiment, the polyurethaneureas used in accordance with the invention are prepared using components A) to H) in the following amounts, where the individual amounts always add up to 100% by weight:
- 10% to 35% by weight of component A),
- 60% to 85% by weight of the sum total of components B) and optionally F),
- 1% to 15% by weight of the sum total of components C1) and optionally E),
- 0.5% to 4% by weight of component C2),
- 0% to 10% by weight of component D),
- 0.3% to 10% by weight of component G) and
- 0.1% to 3% by weight of component H)

In a further preferred embodiment of the invention, the contact-adhesive product comprises a polyurethaneurea obtainable by reaction of at least
- A) one aliphatic polyisocyanate component having an average isocyanate functionality of ≥1.8 and ≤2.6, selected from HDI, IPDI and/or H12-MDI or modification products thereof,
- B) one polymeric polyetherpolyol component, preferably consisting of poly(tetramethylene glycol) polyetherpolyols (such as (HO—(CH$_2$—CH$_2$—CH$_2$—CH$_2$'O)$_x$—H),
- C) one amino-functional chain extender component having at least 2 isocyanate-reactive primary and/or secondary amino groups, containing at least one amino-functional compound C1) that does not have any ionic or ionogenic groups and/or an amino-functional compound C2) that has ionic or ionogenic groups,
- D) optionally further hydrophilizing components different than C2),
- E) optionally hydroxy-functional compounds having a molecular weight of 62 to 399 mol/g,
- F) optionally further polymeric polyols different than B), G) one compound having exactly one isocyanate-reactive group or one compound having more than one isocyanate-reactive group, where only one of the isocyanate-reactive groups reacts with the isocyanate groups present in the reaction mixture under the reaction conditions chosen, and H) optionally one aliphatic polyisocyanate component having an average isocyanate functionality of >2.6 and ≤4, where component H) consists of an aliphatic or cycloaliphatic polyisocyanate oligomer having isocyanurate, urethane, allophanate, biuret, iminooxadiazinedione or oxadiazinetrione structure, wherein components B) and F) together contain ≤30% by weight of component F), based on the total mass of components B) and F), and components G) and H) are present in a relative molar ratio of 1.5:1 to 1:4.

In a particularly preferred embodiment of the invention, the contact-adhesive product comprises a polyurethaneurea obtainable by reaction of at least A) one aliphatic polyisocyanate component which is a mixture of IPDI and HDI, B) one polymeric polyetherpolyol component which is a mixture of at least two poly(tetramethylene glycol) polyetherpolyols and where the poly(tetramethylene glycol) polyetherpolyols differ in their number-average molecular weights, C) one amino-functional chain extender component having 2 isocyanate-reactive primary and/or secondary amino groups, containing at least one amino-functional compound C1) that does not have any ionic or ionogenic groups and/or an amino-functional compound C2) that has ionic or ionogenic groups, D) optionally further hydrophilizing components that are different than C2), which are nonionically hydrophilizing components D1), E) optionally hydroxy-functional compounds having a molecular weight of 62 to 399 mol/g, F) optionally further polymeric polyols different than B), G) one compound having exactly one isocyanate-reactive group or one compound having more than one isocyanate-reactive group, where only one of the isocyanate-reactive groups reacts with the isocyanate groups present in the reaction mixture under the reaction conditions chosen, where the isocyanate-reactive group is a primary and/or secondary amino and/or hydroxyl group, and H) optionally one aliphatic polyisocyanate component having an average isocyanate functionality of >2.6 and ≤4, where component H) consists of an aliphatic or cycloaliphatic polyisocyanate oligomer having isocyanurate, urethane, allophanate, biuret, iminooxadiazinedione or oxadiazinetrione structure, based on HDI, IPDI and/or H12-MDI, wherein components B) and F) together contain ≤30% by weight of component F), based on the total mass of components B) and F), and components G) and H) are present in a relative molar ratio of 1:1 to 1:3.

Most preferably, the polyurethaneurea of the invention is obtainable by reacting exclusively components A) to H). In that case, no further components are used for preparation of the polyurethaneurea.

The polyurethaneureas of the invention are preferably linear molecules, but may alternatively also be branched.

The number-average molecular weight of the polyurethaneureas used with preference in accordance with the invention is preferably from ≥2000 to ≤300 000 g/mol, preferably from ≥5000 to ≤150 000 g/mol.

The polyurethaneurea of the invention is preferably amorphous and has a $T_g$ of ≤−25° C., or preferably of ≤−50° C., or preferably of ≤−70° C.

The polyurethaneurea of the invention is preferably in a physiologically acceptable medium.

The medium is more preferably water, and the polyurethaneurea is most preferably in the form of an aqueous dispersion. In general, alongside other liquid media that are optionally present, for example solvents, water forms the main constituent (>50% by weight) of the dispersion medium, based on the total amount of the liquid dispersion medium, and possibly even the sole liquid dispersion medium.

The aqueous polyurethaneurea dispersions obtained preferably have a content of volatile organic compounds (VOCs), for example volatile organic solvents, of less than 10% by weight, more preferably of less than 3% by weight, even more preferably of less than 1% by weight, based on the aqueous polyurethaneurea dispersion. VOCs in the context of this invention are especially organic compounds having an initial boiling point of at most 250° C. at a standard pressure of 101.3 kPa.

In the context of the present invention, the content of volatile organic compounds (VOCs) is especially determined by gas chromatography analysis.

The pH of the aqueous polyurethane dispersions is typically less than 8.0, preferably less than 7.5, and is more preferably between 5.5 and 7.5.

In order to achieve good sedimentation stability, the number-average particle size of the specific polyurethaneurea dispersions is preferably less than 750 nm, more preferably less than 500 nm, determined by means of laser correlation spectroscopy after dilution with deionized water (instrument: Malvern Zetasizer 1000, Malvern Inst. Limited).

The solids content of the polyurethaneurea dispersions is preferably 10% to 70% by weight, more preferably 20% to 60% by weight and most preferably 40% to 60% by weight. The solids contents are ascertained by heating a weighed sample to 125° C. to constant weight. At constant weight, the solids content is calculated by reweighing the sample.

Preferably, these polyurethaneurea dispersions include less than 5% by weight, more preferably less than 0.2% by weight, based on the mass of the dispersions, of unbound organic airlines.

The polyurethaneurea dispersion has, at a constant shear rate of 10 s$^{-1}$, preferably a viscosity of ≥1 and ≤10 000 mPa s, more preferably of ≥10 and ≤5000 mPa s and most preferably of ≥100 and ≤4000 mPa s. The viscosity is determined as described in the Methods section.

Preferably, the polyurethaneurea used is therefore dispersible in water, which means in the context of this invention that the polyurethaneurea at 23° C. can form a sedimentation-stable dispersion in water, especially deionized water.

The polyurethaneurea of the invention is preferably obtainable by preparing isocyanate-functional polyurethane prepolymers a) from components A), H), B) and optionally D) and/or C2), and optionally compounds E) (step a), and the free NCO groups thereof are then wholly or partially reacted with the amino-functional chain-extender component C), and also component G) and optionally component D) (step b)). Component H) can also not be used until step b), but this is less preferred. When component H) is not used until step b), it is preferably added prior to the addition of component C) and reacted with the prepolymer a).

Components A) to H) are defined here as specified above, and the abovementioned embodiments including all areas of preference are applicable to the preparation process too.

The invention therefore likewise provides a process for preparing the polyurethaneurea of the invention, in which isocyanate-functional polyurethane prepolymers a) are prepared from components A), H), B) and optionally D) and/or C2), and optionally compounds E) (step a), and the free NCO groups thereof are then wholly or partially reacted with the amino-functional chain-extender component C), and also component G) and optionally component D) (step b)). Component H) can also not be used until step b, but this is less preferred. When component H) is not used until step b), it is preferably added prior to the addition of component C) and reacted with the prepolymer a).

Components A) to H) are likewise defined here as specified above, and the abovementioned embodiments including all areas of preference are applicable to the preparation process too.

In a preferred embodiment, components A) and H) are used in already premixed form in s p a).

The invention likewise provides an adhesive, preferably a contact adhesive, comprising the polyurethaneurea of the invention.

The invention further provides an object produced by bonding two or more substrates by means of the polyurethaneurea of the invention or the adhesive of the invention.

Suitable substrates are preferably textile materials, sheet-like substrates made of metal, glass, ceramic, concrete, natural rock, leather, natural fibers and plastics such as PVC, polyolefins, polyurethane or the like. Three-dimensional structures are also suitable as substrates. Particular preference is given to the substrates detailed above for the contact-adhesive product.

An object of the invention may be a mode of transport such as a car, a motorbike, an aircraft, a train; a truck or a bicycle; an electrical article such as a mobile phone or a computer; a building; an item of furniture; a conveyor belt, a construction machine, packaging material, tool, an office article, an item of clothing, a shoe, a domestic article, a medical technology article; where the bond may also relate to individual or multiple parts of the objects mentioned.

The invention further provides an aqueous dispersion comprising a polyurethaneurea of the invention.

The invention further provides for the use of the polyurethaneurea or contact adhesive of the invention for production of contact-adhesive substrates, for example adhesive tapes for domestic or professional use, and for industrial use.

The invention further provides for the use of the polyurethaneurea or contact adhesive of the invention for production of plasters, dressings, tapes or bandages.

The present invention is elucidated by the examples which follow.

EXAMPLES

Methods:

Unless indicated otherwise, all percentages are based on weight and the total amount or on the total weight of the compositions.

Unless stated otherwise, all analytical measurements relate to measurements at temperatures of 23° C.

Solids contents were ascertained in accordance with DIN EN ISOL 3251 by heating a weighed sample to 105° C. to constant weight. At constant weight, the solids content was calculated by reweighing the sample.

Unless explicitly mentioned otherwise, NCO values were determined by lumetric means to DIN-EN ISO 11909.

The check for free NCO groups was conducted by means of IR spectroscopy (hand at 2260 $cm^{-1}$).

The viscosities reported were determined by means of rotary viscometry to DIN 53019 at 23° C. with a rotary viscometer from Anton Paar Germany GmbH, Ostfildern, DE (1 Pa s=1 $N/m^2 \ast s$).

Average particle sizes (the number-average is specified) of the polyurethane dispersions were determined after dilution with deionized water by means of laser correlation spectroscopy (instrument: Malvern Zetasizer 1000, Malvern Inst. Limited).

The pH was measured by the method described in DIN ISO 976 on the undiluted sample.

Glass transition temperature $T_g$ was determined by dynamic differential calorimetry (DSC) in accordance with DIN EN 61006, Method A, using a DSC instrument (Perkin-Elmer Pyris Diamond DSC calorimeter) calibrated with indium and lead for determination of $T_g$. 10 mg of the substance to be analyzed are weighed into a sealable aluminum crucible, which is sealed. Three directly successive runs of a heating operation from −100° C. to +150° C., at a heating rate of 20 K/min, with subsequent cooling at a cooling rate of 320 K/min are undertaken, and the third heating curve is used to determine the values. $T_g$ is the temperature determined at half the height of a glass transition step.

The air permeability of the substrates in the unstretched state was determined to DIN EN ISO 9237.

The maximum tensile force of the substrates was determined by a tensile strip test according to DIN EN ISO 13934-1.

The stretching range of the substrates was determined by determining the tensile characteristics of the substrates by means of repeated tensile stress between constant extension limits, and the determination of the total extension to DIN 53835 Part 2.

Substances and Abbreviations Used:

| | |
|---|---|
| Diaminosulfonate: | $NH_2$—$CH_2CH_2$—NH—$CH_2CH_2$—$SO_3Na$ (45% in water) |
| PolyTHF 1000 | poly(tetramethylene glycol) polyetherdiol having number-average molar mass 1000 g/mol, BASF SE, Ludwigshafen, DE |
| PolyTHF 2000 | poly(tetramethylene glycol) polyetherdiol having number-average molar mass 2000 g/mol, BASF SE, Ludwigshafen, DE |
| Water | water demineralized by ion exchanger |

The isocyanate components used are commercial products from Covestro Deutschland AG, Leverkusen, DE. Further chemicals were purchased from Sigma-Aldrich Chemie GmbH, Taufkirchen, DE. Unless stated otherwise, the raw materials were used without further purification or pretreatment.

Inventive Polyurethaneurea Dispersion 1

360 g of PolyTHF® 1000 and 1680 g of PolyTHF® 2000 were heated to 70° C. Subsequently, a mixture of 180.6 g of hexamethylene diisocyanate and 238.7 g of isophorone diisocyanate was added, and the mixture was stirred at 100-115° C. until the NCO value had eone below the theoretical value. The finished prepolymer was dissolved with 4400 g of acetone at 50° C. and then a solution of 19.6 g of ethylenediamine, 86.3 g of diaminosulfonate, 27.9 g of diethanolamine and 380 g of water was metered in. The mixture was stirred for a further 15 min. This was followed by dispersion by addition of 2100 g of water. Subsequently, the solvent was removed by distillation under reduced pressure, and a storage-stable dispersion was obtained; the solids content was adjusted by addition of water.

Solids content: 52%
Particle size (LKS): 292 nm
Viscosity: 440 mPa s
Tg of polyurethaneurea: −78.7° C.

Inventive Polyurethaneurea Dispersion 2

75 g of PolyTHF® 1000 and 350 g of PolyTHF® 2000 were heated to 70° C. Subsequently, a mixture of 33.9 g of hexamethylene diisocyanate, 49.7 g of isophorone diisocyanate and 8.7 g of Desmodur N 3300 (HDI trimer having an NCO content of about 21.8% to DIN EN ISO 11 909) was added, and the mixture was stirred at 100-115° C. until the NCO value had gone below the theoretical value. The finished prepolymer was dissolved with 920 g of acetone at 50° C. and then a solution of 3.2 g of ethylenediamine, 12.9 g of diaminosulfonate, 11.7 g of diethanolamine and 145 g of water was metered in. The mixture was stirred for a further 15 min. This was followed by dispersion by addition of 1080 g of water. Subsequently, the solvent was removed by distillation under reduced pressure, and a storage-stable dispersion was obtained; the solids content was adjusted by addition of water.

Solids content: 52%
Particle size (LKS): 307 nm
Viscosity: 105 mPa s
Tg of polyurethaneurea: −78.0° C.

Polyurethaneurea Dispersion C1 (Comparison 1)

450 g of PolyTHF® 1000 and 2100 g of PolyTHF® 2000 were heated to 70° C. Subsequently, a mixture of 225.8 g of hexamethylene diisocyanate and 298.4 g of isophorone diisocyanate was added, and the mixture was stirred at 100-115° C. until the NCO value had gone below the theoretical value. The finished prepolymer was dissolved with 5460 g of acetone at 50° C. and then a solution of 29.5 g of ethylenediamine, 143.2 g of diaminosulfonate and 610 g of water was metered in. The mixture was stirred for a further 15 min. This was followed by dispersion by addition of 1880 g of water. Subsequently, the solvent was removed by distillation under reduced pressure, and a storage-stable dispersion was obtained; the solids content was adjusted by addition of water.

Solids content: 56%
Particle size (LKS): 276 nm
Viscosity: 1000 mPas
Tg of polyurethaneurea: −79.1° C.

Polyurethane Dispersion C2 According to U.S. Pat. No. 5,692,937 (Comparision 2)

The polyurethane dispersion described in U.S. Pat. No. 5,692,937 example 1 (column 4 lines 15 to 34) was reworked. This was done using the IPDI and the polyols from Covestro AG, Leverkusen, Del., while all other chemicals were sourced from Sigma-Aldrich Chemie GmbH, Taufkirchen, Del.

The polyurethane dispersions from the comparative examples were prepared in apparatuses and under conditions comparable to those in U.S. Pat. No. 5,692,937 and the inventive examples.

Use Tests:
Materials Used:
Ypsiflex bandage from Holthaus Ref. 12906S: Air permeability in the unstretched state: 5548 f/m2*s, stretching range: 160%, maximum tensile force: 155.9 N;
Ypsifix bandage from Holthaus Ref. 12223

Testing of Contact Tack:

After the polyurethaneurea composition has been applied and dried to a 30 cm-long Ypsifix bandage (Ref. 12223) or Ypsiflex bandage (Ref 12906S), it is bound around a pin such that the windings are one on top of another. After 14 days, the contact adhesion force of the product to itself is examined. This is done by placing two pieces of length 3 cm one on top of the other, using fingers to gently press them together at room temperature for 10 s, and directly thereafter visually ascertaining the detachment characteristics by pulling the two pieces apart. The scale assessment ranges from 1 (no sticking together) to 5 (sticking very firmly together). Contact tack is considered to be sufficient over and above a classification of "3".

Use Example A1 (Inventive)

97 g of inventive polyurethaneurea dispersion 1 was initially charged together with 3 g of glycerol in a Speedmixer cup. Bubble-free mixing to give a polyurethaneurea composition was effected in the Speedmixer at a speed of 2750 min$^{-1}$ for 1 minute. For the spray experiment that followed, the Holthaus Ypsiflex gauze bandage (Ref. 12906S) (6×30 cm$^2$) (substrate) that was to be wetted was fixed in a rigid frame. The formulation was transferred from the Speedmixer cup into the reservoir of a spray gun (SATA Jet RP Digital). By means of an air pressure of 1.5 bar, the polyurethaneurea composition was distributed in droplet form onto the substrate via a nozzle (diameter 1.6 mm). The substrate was sprayed once from each side. Drying at 100° C. in an air circulation drying cabinet for 10 min was preceded by predrying at RT for 20 min. After drying, the 30 cm-long coated bandage is wound around a pin such that the windings were one on top of another. The coated bandage stuck together only slightly in the wound arrangement, and did not bond even after storage for 14 days. Contact tack was assessed after 14 days and is listed in table 1.

Use Example A2 (Comparison)

97 g of the comparative polyurethaneurea dispersion C1 was initially charged together with 3 g of glycerol in a Speedmixer cup. Bubble-free mixing to give a polyurethaneurea composition was effected in the Speedmixer at a speed of rotation of 2750 min$^{-1}$ for 1 minute. For the spray experiment, the Holthaus Ypsiflex gauze bandage (Ref. 12906S) (6×30 cm$^2$) (substrate) that was to be wetted was fixed in a rigid frame. The formulation was transferred from the Speedmixer cup into the reservoir of a spray gun (SATA Jet RP Digital). By means of an air pressure of 1.5 bar, the polyurethaneurea composition was distributed in droplet form onto the substrate via a nozzle (diameter 1.6 mm). The substrate was sprayed once from each side. Drying at 100° C. in an air circulation drying cabinet for 10 min was preceded by predrying at RT for 20 min. After drying, the 30 cm-long coated bandage was wound around a pin such that the windings were one on top of another. Contact tack was assessed after 14 days and is listed in table 1.

Use Example A3 (Inventive)

For the spray experiment, the Ypsifix gauze bandage (Ref. 12223) (6×30 cm$^2$) (substrate) that was to be wetted was fixed in a rigid frame. 100 g of the untreated inventive polyurethaneurea dispersion 2 were transferred into the reservoir of a spray gun (SATA Jet RP Digital). By means of an air pressure of 1.5 bar, the dispersion was distributed in droplet form onto the substrate via a nozzle (diameter 1.6 mm). The substrate was sprayed once from each side. Drying was effected at 100° C. in air circulation drying cabinet for 60 min. After drying, the 30 cm-long coated bandage was wound around a pin such that the windings were one on top of another. The coated bandage stuck together only slightly in the wound arrangement, and did not bond even after storage for 14 days. Contact tack was assessed after 14 days and is listed in table 1.

Use Example A4 (Inventive)

180 g of the inventive polyurethaneurea dispersion 1 were blended with 0.9 g of Rheolate 678 by means of a precision glass stirrer (speed: 1100 min$^{-1}$ and stirring time: 5 min) to give a polyurethaneurea composition. The Ypsiflex bandage (Ref.12906S) (6×30 cm$^2$) (substrate) to be wetted was fixed in a stretcher of a Mathis oven. The polyurethaneurea composition produced was applied in the upper part of the fixed textile and then distributed homogeneously by drawing a coating bar over it. The coating bar gap was 100 μm. Drying was effected in the Mathis oven at 120° C. for 2 min. The contact tack of the unrolled bandage was tested after 14 days and is listed in table 1.

Use Example A5 (Comparison)

For the spray experiment, the Ypsiflex gauze bandage (Ref. 12906S) (6×30 cm$^2$) (substrate) that was to be wetted was fixed in a rigid frame. 100 g of the untreated comparative polyurethaneurea dispersion C2 were transferred into the reservoir of a spray gun (SATA Jet RP Digital). By means of an air pressure of 1.5 bar, the dispersion was distributed in droplet form onto the substrate via a nozzle (diameter 1.6 mm). The substrate was sprayed once from each side. Drying at 100° C. in an air circulation drying cabinet for 10 min was preceded by predrying at RT for 20 min. After drying, the 30 cm-long coated bandage was wound around a pin such that the windings were one on top of another. Contact tack was assessed after 14 days and is listed in table 1.

TABLE 1

Test of contact tack after 14 days:

| After 14 days | Example A1 | Example A2 (comparative) | Example A3 | Example A4 | Example A5 (comparative) |
| --- | --- | --- | --- | --- | --- |
| Assessment | 3 | 1 | 4 | 3 | 1-2 |

Test of Discoloration:

The color values (L, a and b as per CIELab system) were determined on films of layer thickness 100 μm that had been produced on 20 cm*10 cm glass plates of thickness 3 mm from Glas & Fenster Engelbrecht GmbH, Leiehlingen (Rhineland), Germany (application with an applicator frame of gap width 200 μm and subsequent drying). The measurement of layer thickness was ascertained with a compressed air gauge connected to a display from Heidehain (MT25P) to display the layer thickness. A thickener was added to all formulations for better film formation (0.5% by weight to 100% by weight of dispersion).

The color value was measured in transmission with the Konica Minolta CMS instrument, the color values were calculated to DIN 11664-4, and the measurement geometry was fixed according to DIN 5033-7 with the parameters d/8, D65 and SCi. The b value describes the yellow color of a film. Table 2 lists test results. The measurement was conducted about 10 days after production of the films. The deviation in the thickness of the films was only a maximum of 1%, based on the thickest point in the film.

It is apparent that the b values of the inventive samples have distinctly lower discoloration compared to the comparative samples. Particularly the aliphatic isocyanates, unlike aromatic isocyanates, are not light-sensitive. While aromatic isocyanates show yellow discoloration on exposure to sunlight, aliphatic isocyanates do not show any discoloration at all through UV radiation such as sunlight.

Formulations used for the color measurement:

Use Example A6 ((Inventive), Corresponding to A1 and A4)

100 g of inventive polyurethaneurea dispersion 1 were initially charged together with 3 g of glycerol and 0.5 g of Rheolate 210 in a Speedmixer cup. Bubble-free mixing to give a polyurethaneurea composition was effected in the Speedmixer at a speed of 2750 min$^{-1}$ for 1 minute. After application by means of a coating bar, drying at 50° C. for 10 min and at 120° C. for 3 min in an air circulation drying cabinet was preceded by predrying at RT for 20 min.

Use Example A7 ((Comparison), Corresponding to A2)

100 g of comparative polyurethaneurea dispersion C1 were initially charged together with 3 g of glycerol and 0.5 g of Rheolate 210 in a Speedmixer cup. Bubble-free mixing to give a polyurethaneurea composition was effected in the Speedmixer at a speed of 2750 min$^{-1}$ for 1 minute. After application by means of a coating bar, drying at 50° C. for 10 min and at 120° C. for 3 min in an air circulation drying cabinet was preceded by predrying at RT for 20 min.

Use Example A8 ((Inventive), Corresponding to A3)

100 g of inventive polyurethaneurea dispersion 2 were initially charged together with 0.5 g of Rheolate 210 in a Speedmixer cup. Bubble-free mixing to give a polyurethaneurea composition was effected in the Speedmixer at a speed of 2750 min$^{-1}$ for 1 minute. After application by means of a coating bar, drying at 50° C. for 10 min and at 120° C. for 3 min in an air circulation drying cabinet was preceded by predrying at RT for 20 min.

Use Example A9 ((Comparison), Corresponding to A5)

100 g of comparative polyurethaneurea dispersion C2 were initially charged together with 0.5 g of Rheolate 210 in a Speedmixer cup. Bubble-free mixing to give a polyurethaneurea composition was effected in the Speedmixer at a speed of 2750 min$^{-1}$ for 1 minute. After application by means of a coating bar, drying at 50° C. for 10 min and at 120° C. for 3 min in an air circulation drying cabinet was preceded by predrying at RT for 20 min.

TABLE 2

Measurement of color values:

|  | Example A6 | Example A7 (comparative) | Example A8 | Example A9 (comparative) |
|---|---|---|---|---|
| Layer thickness (μm) | 73 | 98 | 87 | 83 |
| L value | 96.6 | 96.6 | 96.6 | 96.4 |
| a value | −0.5 | −0.5 | −0.5 | −0.6 |
| b value | 0.3 | 0.2 | 0.3 | 1.0 |

The invention claimed is:

1. A contact-adhesive product comprising a substrate and a polyurethaneurea obtained by reacting at least
   A) one aliphatic polyisocyanate component having an average isocyanate functionality of ≥1.8 and ≤2.6,
   B) one polymeric polyetherpolyol component,
   C) one amino-functional chain extender component having at least 2 isocyanate-reactive amino groups, containing at least one amino-functional compound C1) that does not have any ionic or ionogenic groups and/or an amino-functional compound C2) that has ionic or ionogenic groups,
   D) optionally further hydrophilizing components different than C2),
   E) optionally hydroxy-functional compounds having a molecular weight of 62 to 399 mol/g,
   F) optionally at least one further polymeric polyol different than B),
   G) one compound having exactly one isocyanate-reactive group or one compound having more than one isocyanate-reactive group, where only one of the isocyanate-reactive groups reacts with the isocyanate groups present in the reaction mixture under the reaction conditions chosen, and
   H) optionally one aliphatic polyisocyanate component having an average isocyanate functionality of >2.6 and ≤4,
   wherein components B) and F) together contain ≤30% by weight of component F), based on the total mass of components B) and F).

2. The product as claimed in claim 1, characterized in that component A) is isophorone diisocyanate and/or hexamethylene diisocyanate.

3. The product as claimed in claim 1, characterized in that component B) contains or consists of poly(tetramethylene glycol) polyetherpolyols (such as (HO—(CH$_2$—CH$_2$—CH$_2$—CH$_2$—O)$_x$—H).

4. The product as claimed in claim 1, characterized in that component B) contains or consists of a mixture of poly(tetramethylene glycol) polyetherpolyols, wherein the poly(tetramethylene glycol) polyetherpolyols differ in their number-average molecular weights.

5. The product as claimed in claim 1, characterized in that component D) comprises nonionically hydrophilizing components.

6. The product as claimed in claim 1, characterized in that component H) is used and the molar ratio of component G) to component H) is 5:1 to 1:5.

7. The product as claimed in claim 1, characterized in that the polyurethaneurea is obtained by preparing isocyanate-functional polyurethane prepolymers a) from components A), B) and optionally D) and/or C2), and optionally compounds E) and/or H), and the free NCO groups thereof are then wholly or partially reacted with the amino-functional chain-extender component C), and also component G) and optionally components D) and H).

8. The product as claimed in claim 1, characterized in that the polyurethaneurea is amorphous and has a Tg≤−25° C., determined by means of dynamic differential calorimetry in accordance with DIN EN 61006, Method A.

9. The product as claimed in claim 1, characterized in that the substrate has a maximum tensile force of 100 to 500 N, determined to DIN EN ISO 13934-1.

10. The product as claimed in claim 1, characterized in that the product is a plaster, a dressing, a tape or a bandage or at least a constituent of these end products.

11. A process for producing a contact-adhesive product as claimed in claim 1, comprising the steps of
   I) applying the polyurethaneurea to the substrate in the form of an aqueous polyurethaneurea dispersion and
   II) thermally drying the treated substrate at temperatures ≥20° C. and ≤200° C.

12. A polyurethaneurea obtained by reacting at least
   A) one aliphatic polyisocyanate component having an average isocyanate functionality of ≥1.8 and ≤2.6,
   B) one polymeric polyetherpolyol component,
   C) one amino-functional chain extender component having at least 2 isocyanate-reactive amino groups, containing at least one amino-functional compound C1) that does not have any ionic or ionogenic groups and/or an amino-functional compound C2) that has ionic or ionogenic groups,
   D) optionally further hydrophilizing components different than C2),
   E) optionally hydroxy-functional compounds having a molecular weight of 62 to 399 mol/g,
   F) optionally further polymeric polyols different than B),
   G) one compound having exactly one isocyanate-reactive group or one compound having more than one isocyanate-reactive group, where only one of the isocyanate-reactive groups reacts with the isocyanate groups present in the reaction mixture under the reaction conditions chosen, and
   H) one aliphatic polyisocyanate component having an average isocyanate functionality of >2.6 and ≤4,
   wherein components B) and F) together contain ≤30% by weight of component F), based on the total mass of components B) and F), and components G) and H) are present in a relative molar ratio of 5:1 to 1:5.

13. An adhesive comprising a polyurethaneurea as claimed in claim 12.

14. An object produced by bonding two or more substrates by means of a polyurethaneurea as claimed in claim 12.

15. An aqueous dispersion comprising a polyurethaneurea as claimed in claim 12.

* * * * *